United States Patent
Ohama

(10) Patent No.: US 10,369,374 B2
(45) Date of Patent: Aug. 6, 2019

(54) MAGNETIC HEALTH DEVICE AND METHOD OF USING MAGNETIC HEALTH DEVICE

(71) Applicant: Haruo Ohama, Tokyo (JP)

(72) Inventor: Haruo Ohama, Tokyo (JP)

( * ) Notice: Subject to any disclaimer, the term of this patent is extended or adjusted under 35 U.S.C. 154(b) by 246 days.

(21) Appl. No.: 15/312,009

(22) PCT Filed: May 11, 2015

(86) PCT No.: PCT/JP2015/002377
§ 371 (c)(1),
(2) Date: Nov. 17, 2016

(87) PCT Pub. No.: WO2015/177981
PCT Pub. Date: Nov. 26, 2015

(65) Prior Publication Data
US 2017/0120068 A1 May 4, 2017

(30) Foreign Application Priority Data
May 19, 2014 (JP) ................................. 2014-103431

(51) Int. Cl.
*A61N 2/12* (2006.01)
(52) U.S. Cl.
CPC ...................................... *A61N 2/12* (2013.01)
(58) Field of Classification Search
CPC ............... A61N 2/00; A61N 2/06; A61N 2/12
See application file for complete search history.

(56) References Cited

U.S. PATENT DOCUMENTS

| 6,648,812 | B2 | 11/2003 | Ardizzone |
| 7,507,198 | B2 | 3/2009 | Ardizzone |
| 2002/0147380 | A1 | 10/2002 | Ardizzone |
| 2003/0083537 | A1* | 5/2003 | Ardizzone ............... A61N 2/12 600/9 |
| 2004/0106843 | A1 | 6/2004 | Ardizzone |

(Continued)

FOREIGN PATENT DOCUMENTS

| EP | 0040053 B1 | 11/1984 |
| EP | 0253398 A1 | 1/1988 |
| JP | S62-99254 | 6/1987 |

(Continued)

OTHER PUBLICATIONS

Translation of written opinion of PCT/JP2015/002377 corresponding to JP2014-103431 dated Aug. 4, 2015 (6 Sheets).

(Continued)

*Primary Examiner* — Carrie R Dorna
(74) *Attorney, Agent, or Firm* — Kratz, Quintos & Hanson, LLP

(57) ABSTRACT

To provide a magnetic health device capable of making a variable magnetic field to effectively act. The magnetic health device includes a magnet 12 magnetized along a rotation direction, a first rotation mechanism 13 which rotates the magnet 12 around a rotation shaft 31 of the magnet 12, a second rotation mechanism 14 which rotates the magnet 12 around an orthogonal axis direction of the rotation shaft 31 of the magnet 12, and a support means 15 for supporting the magnet 12, the first rotation mechanism 13 and the second rotation mechanism 14 with respect to a human body.

2 Claims, 3 Drawing Sheets

(56) References Cited

U.S. PATENT DOCUMENTS

2005/0124847 A1 6/2005 Ardizzone

FOREIGN PATENT DOCUMENTS

| | | |
|---|---|---|
| JP | H1-34629 B2 | 7/1989 |
| JP | H3-1009 Y2 | 1/1991 |
| JP | H10-192421 A | 7/1998 |
| JP | 2002-65870 A1 | 3/2002 |
| JP | 2005-518884 A1 | 6/2005 |
| JP | 3193640 U | 10/2014 |
| WO | 2003074124 A1 | 9/2003 |
| WO | 2013173235 A1 | 11/2013 |

OTHER PUBLICATIONS

Japanese Office Action for JP2014-103431 dated Jan. 23, 2018 (6 Sheets).
Written Opinion of the International Searching Authority for International Application No. PCT/JP2015/002377 dated Aug. 4, 2015 (4 Sheets, 2 Sheets translation; 6 Sheets total)/Concise explanation of JP documents S62-99254 and 2002-65870.
International Search Report for International Application No. PCT/JP2015/002377 dated Aug. 4, 2015.
Extended European Search Report for counterpart EPC Patent Application No. 15796342.2 dated Dec. 14, 2017 (7 Sheets).

* cited by examiner

MAGNETIC HEALTH DEVICE AND METHOD OF USING MAGNETIC HEALTH DEVICE

TECHNICAL FIELD

The present invention relates to a magnetic health device utilizing a variable magnetic field and a method of using the magnetic health device

BACKGROUND ART

Due to the progress of study about the influence of magnetism on a human body, a knowledge that a variable magnetic field is more effective than a steady magnetic field for promoting circulation of body fluids such as blood in the human body has been obtained. For example, a rotating magnetic generator for a magnetic health device is disclosed in Patent Literature 1, which gives the effect of promoting circulation of body fluids such as blood in the human body by adding a vibration simultaneously with the variable magnetic field.

CITATION LIST

Patent Literature

Patent Literature 1: JP-A 2001-061976

SUMMARY OF INVENTION

Technical Problem

It is preferable to make the variable magnetic field effectively act on various elements of the human body when using the magnetic health device. Although the magnetic generator disclosed in Patent Literature 1 vibrates in addition to the rotation around a rotation axis, an effective range of the variable magnetic field itself to be formed is limited when the device is arranged in particular positions and the effect is not sufficient. Accordingly, a trouble of changing the position every time may occur for making the magnet field act on various elements.

The present invention has been made in view of the above circumstances, and an object thereof is to provide a magnetic health device and a method of using the magnetic health device capable of allowing the variable magnetic field to act effectively.

Solution to Problem

A magnetic health device of the present invention includes a magnet magnetized along a rotation direction, a first rotation mechanism which rotates the magnet around a rotation shaft of the magnet, a second rotation mechanism which rotates the magnet around an orthogonal axis direction of the rotation shaft of the magnet and a support means for supporting the magnet, the first rotation mechanism and the second rotation mechanism with respect to a human body.

A method of using a magnetic health device of the present invention includes the steps of a first rotation step of rotating a magnet magnetized along a rotation direction around a rotation shaft of the magnet, a second rotation step of rotating the magnet around an orthogonal axis direction of the rotation shaft of the magnet and a support step of supporting the magnet with respect to a human body.

Advantageous Effects of Invention

In the magnetic health device and the method of using the magnetic health device according to the present invention, it is possible to make a variable magnetic field efficiently act.

DESCRIPTION OF EMBODIMENTS

A magnetic health device and a method of using the magnetic health device according to an embodiment of the present invention will be explained with reference to the drawings.

Figure 1:
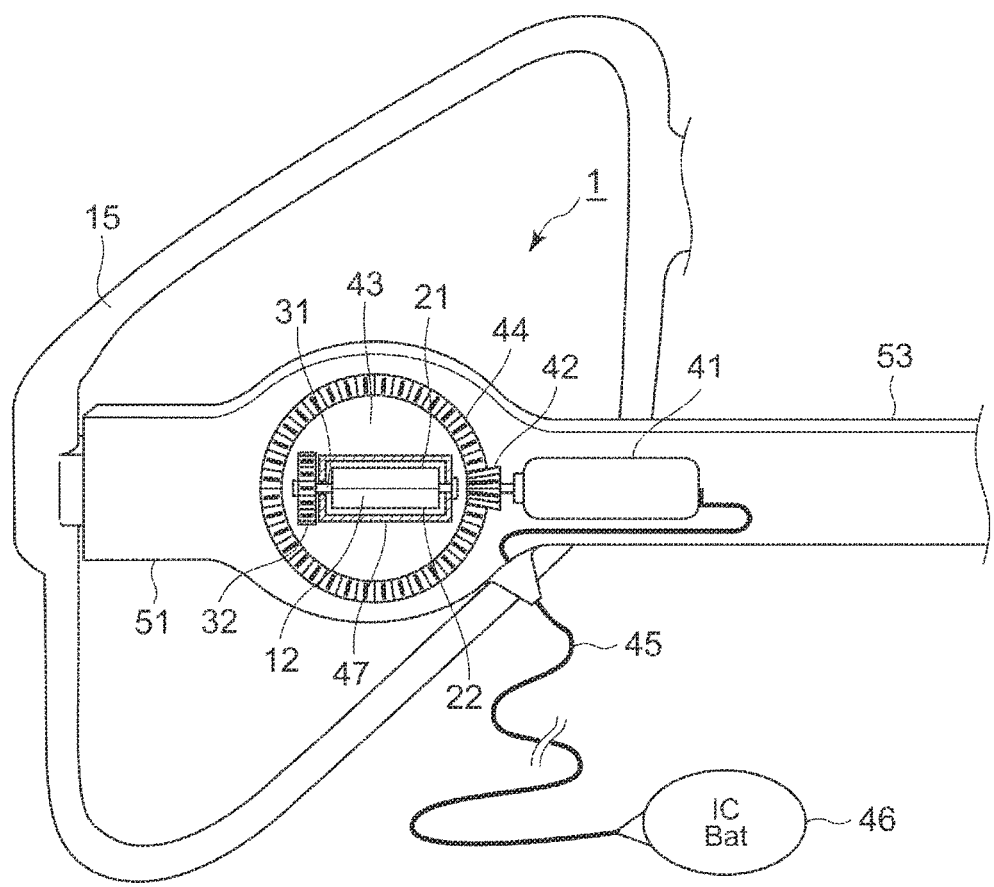
FIG. 1 is an explanatory view showing an internal structure of an inner plate side of a magnetic health device according to an embodiment.

FIG. 1 is an explanatory view showing an internal structure of an inner plate 51 side of a magnetic health device 1 according to the embodiment.

Figure 2:
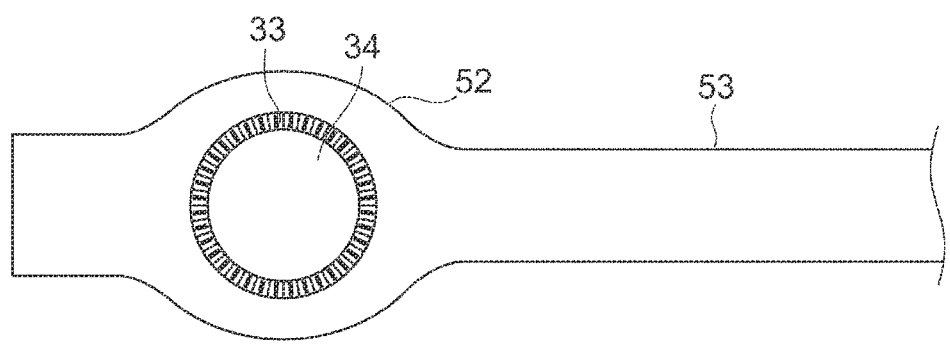
FIG. 2 is an explanatory view of an internal structure of an outer plate side of the magnetic health device.

FIG. 2 is an explanatory view of an internal structure of an outer plate 52 side of the magnetic health device 1.

Figure 3:
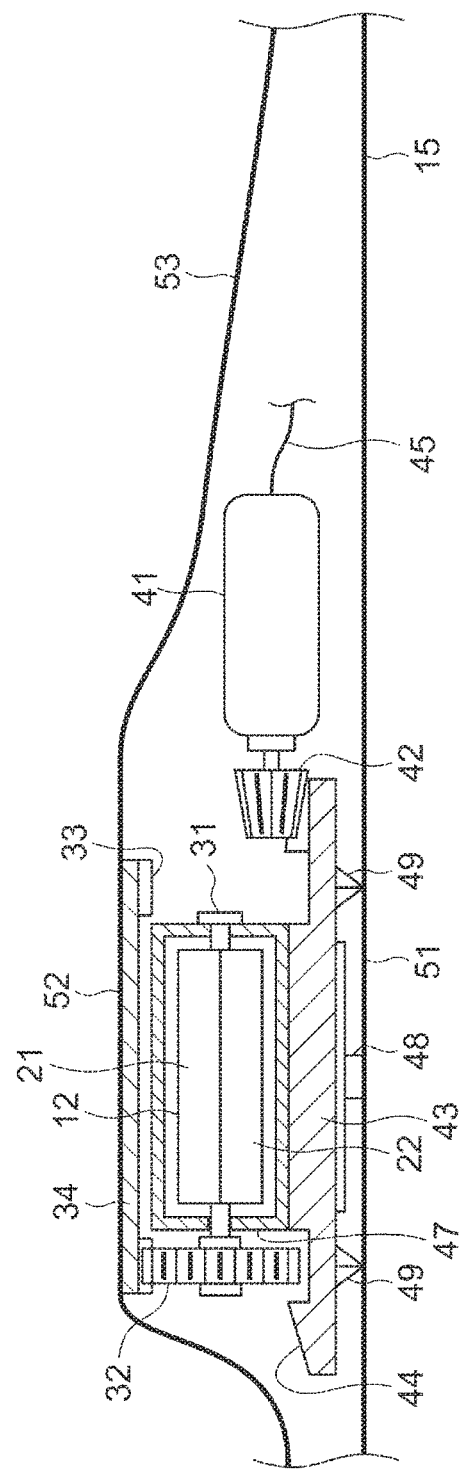
FIG. 3 is an explanatory view showing an internal structure of the magnetic health device, which is cross-sectional view seen from above when the device is worn.

FIG. 3 is an explanatory view showing an internal structure of the magnetic health device 1, which is a partial cross-sectional view seen from above when the device is worn.

Figure 4:
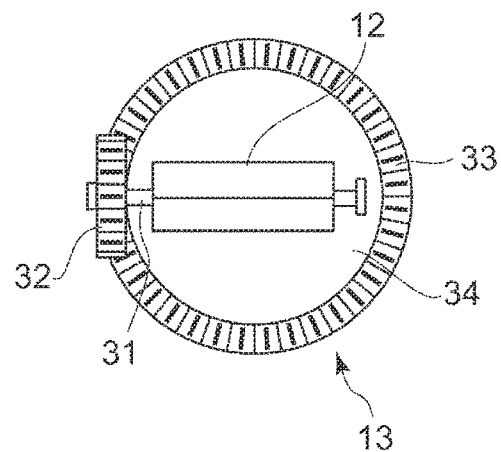
FIG. 4 is a structural diagram for explaining a first rotation mechanism.

FIG. 4 is a structural diagram for explaining a first rotation mechanism 13.

Figure 5:
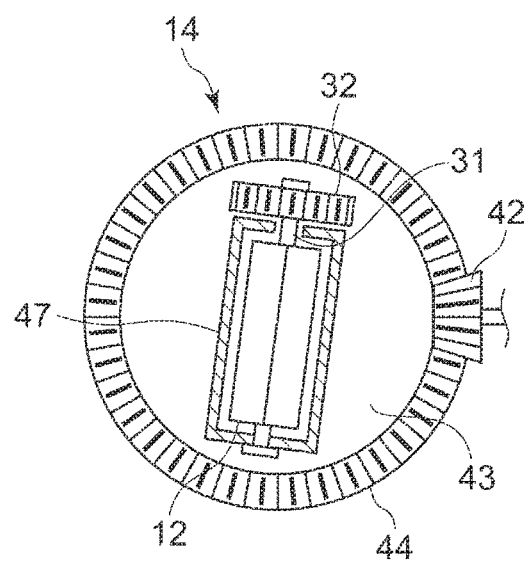
FIG. 5 is a structural diagram explaining a second rotation mechanism 14.

FIG. 5 is a structural diagram for explaining a second rotation mechanism 14.

The magnetic health device 1 according to the embodiment has an outer appearance of a shape of glasses as shown in FIG. 1, which is used by a user being worn like glasses.

The magnetic health device 1 includes a magnet 12, a first rotation mechanism 13, a second rotation mechanism 14 and a frame 15 (support means)

The magnet 12 is a columnar magnet magnetized with an N-pole 21 and an S-pole 22 along the rotation direction. That is, the magnet 12 is divided into two parts by a plane including an axis of the column, and one is magnetized with the N-pole 21 and the other is magnetized with the S-pole 22.

As shown in FIG. 4, the first rotation mechanism 13 rotates the magnet 12 around a rotation shaft 31 of the magnet 12. The rotation shaft 31 is a shaft approximately corresponds to the column axis of the magnet 12. The first rotation mechanism 13 includes a rotation shaft gear 32 (first gear) fixed to the rotation shaft 31 of the magnet 12 and a fixed plate gear 33 (second gear) engaging with the rotation shaft gear 32.

The fixed plate gear 33 is provided in a circumferential direction on an outer edge of a fixed plate 34 as shown in FIG. 2. The fixed plate 34 is a circular member fixed to an outer plate 52 of the frame 15 (temple 53). The rotation shaft gear 32 is fixed to the magnet 12 through the rotation shaft 31. Accordingly, the magnet 12 rotates around the rotation shaft 31 with the movement of the rotation shaft gear 32 on the fixed plate gear 33.

As shown in FIG. 5, the second rotation mechanism 14 rotates the magnet 12 around an orthogonal axis direction (around an approximately orthogonal axis) which is orthogonal to the rotation shaft 31 of the magnet 12. The orthogonal axis corresponds to a horizontal direction (direction connecting the inner side (inner plate 51) of the frame 15 and the outside (outer plate 52)) when the magnetic health device 1 is worn. The second rotation mechanism 14 includes a motor 41, a motor gear 42, a rotating plate 43 and a rotating plate gear 44.

The motor 41 (reduction gear motor) is connected to a battery 46 through a lead wire 45 as shown in FIG. 1, which is driven by power supplied from the battery 46. The battery 46 is also provided with a motor driving IC. The motor gear 42 is a gear provided in the shaft of the motor 41. The rotating plate 43 is a circular member, supporting the magnet 12 so as to rotate around the rotation shaft 31. Specifically, a case 47 housing the magnet 12 is fixed to the rotating plate 43, and the magnet 12 is supported in the case 47 so that the rotation shaft 31 can rotate. The rotating plate 43 is rotatably supported in the inner plate 51 of the frame 15 through a shaft 48. The rotating plate 43 has a support member 49 for supporting the rotation of the rotating plate 43. The rotating plate gear 44 is provided in a circumferential direction on an outer edge of the rotating plate 43, engaging with the motor gear 42. Accordingly, the rotating plate gear 44 rotates around the shaft 48 with the rotation of the motor gear 42. It is preferable to provide a support gear for supporting the motor gear 42 in a direction of the rotating plate gear 44 or to provide a belt for suppressing vibration of the motor 41 in order to secure the engagement between the motor gear 42 and the rotating plate gear 44.

The frame 15 (support means) supports the magnet 12, the first rotation mechanism 13 and the second rotation mechanism 14 on a head of the user. The frame 15 has the shape of glasses having a pair of temples 53, in which the magnet 12, the first rotation mechanism 13 and the second rotation mechanism 14 are supported by the pair of temples 53. Though only part of the frame 15 is shown in FIG. 1, the magnet 12, the first rotation mechanism 13 and the second rotation mechanism 14 are actually provided in each of right and left temples 53, which are supported on both sides of the head of the user.

The magnetic health device 1 according to the embodiment having the above structure rotates the magnet 12 around two axes. That is, the magnetic health device 1 according to the embodiment is used by achieving a first rotation step of rotating the magnet 12 magnetized along the rotation direction around the rotation shaft 31 of the magnet 12, a second rotation step of rotating the magnet 12 around the orthogonal axis direction of the rotation shaft 31 of the magnet 12 and a support step of supporting the magnet 12 to the human body. More specifically, the rotating plate 43 rotates with the rotation of the motor gear 42 and the rotating plate gear 44 due to the rotation of the motor 41. Accordingly, the magnet 12 rotates around the shaft 48 (orthogonal axis of the magnet 12) with the rotating plate 43. The rotation shaft gear 32 rotates and moves on the fixed plate gear 33 with the rotation of the magnet 12 around the shaft 48. Accordingly, the magnet 12 rotates around the rotation shaft 31.

Rotating speeds of the first rotation mechanism 13 and the second rotation mechanism 14 can be arbitrarily set. For example, the rotation of the second rotation mechanism 14, namely, the rotating plate 43 can be set to, for example, 1 rpm. The rotation of the first rotation mechanism 13, namely, the rotation of the rotation shaft gear 32 can be set to, for example, 4 rpm.

The motor 41 may operate intermittently, for example, in a manner in which the motor 41 stops when the rotating plate rotates a certain degree (for example, 45 degrees). Accordingly, power consumption can be effectively reduced.

The magnetic health device 1 according to the embodiment can rotate the magnet 12 around two axes and allows the variable magnetic field to act more effectively. In particular, when the magnets 12 are symmetrically arranged in portions of the temples 53 so that the variable magnetic field acts on both sides of the head, the variable magnetic field is allowed to act more effectively. That is, it is possible to allow an almost radial variable magnetic field to act in a wider range as compared with a case where the magnet rotates only around the rotation shaft 31. There exist many elements particularly in the head, which serve important functions in the human body such as eyes, brains, ears, a nose, skin of a face. Therefore, the head of the human body is preferable as a target in which therapeutic effects of the magnetic health device 1 are achieved. The magnetic health device 1 according to the embodiment can improve circulation of body fluids, in the entire head, which can effectively give therapeutic effects to the eyes, the brains, the ears, the nose, the skin and so on.

For example, the device is considered to have effects on eye diseases such as ametropia of an eye, dry eyes, sinusitis, hay fever, mild deafness, rejuvenation of skin cells and so on.

It is also possible to reduce the size of the magnetic health device 1 by configuring the mechanisms for rotating the magnet 12 in the manner as in the first and second rotation mechanisms 13, 14 according to the embodiment.

Some embodiments of the present invention have been explained, however, these embodiments are cited as examples and are not intended to limit the scope of the invention.

For example, the shape of the support means is not limited to the shape of glasses, and the device may be supported in the head by using a belt or a headdress. The magnetic health device and the method of using the magnetic health device according to the present invention may be applied not only to the head but various places of the human body. Furthermore, the rotation mechanisms are not limited to the first and second rotation mechanisms 13, 14 as long as the magnet 12 can rotate around two axes.

REFERENCE SIGNS LIST 1 magnetic health device
12 magnet
15 frame
21 N-pole
22 S-pole
31 rotation shaft
32 rotation shaft gear
33 fixed plate gear
34 fixed plate
41 motor
42 motor gear
43 rotating plate
44 rotating plate gear
45 lead wire
46 battery 47 case
48 shaft
49 support member
51 inner plate
52 outer plate
53 temple

The invention claimed is:

1. A magnetic health device comprising:
a columnar magnet divided into two parts by a plane including a columnar axis as a rotation shaft, one part being magnetized with a N-pole, the other part being magnetized with a S-pole;
a first rotation mechanism which rotates the magnet around the rotation shaft of the magnet;
a second rotation mechanism which rotates the magnet around an orthogonal axis direction of the rotation shaft of the magnet; and
a frame having a shape of glasses including a pair of temples, configured to support the magnetic health device to a head, at least one of the pair of temples including a first plate and a second plate, the first plate and the second plate housing the magnet, the first rotation mechanism and the second rotation mechanism,
wherein the first rotation mechanism comprises:
a rotation shaft gear fixed to the rotation shaft of the magnet;
a fixed plate being a circular member fixed to the second plate; and
a fixed plate gear provided in a circumferential direction on an outer edge on an opposite surface of the fixed plate from a surface fixed to the second plate,
the second rotation mechanism comprises:
a motor;
a motor gear provided to the motor;
a rotating plate being a circular member, supported by the first plate so as to rotate around the orthogonal axis direction along a direction substantially orthogonal to a surface direction of the first plate, and the rotating plate supporting the magnet so as to rotate around the rotation shaft on an opposite surface of the rotating plate from a surface supported by the first plate; and
a rotating plate gear provided in a circumferential direction on an outer edge of the rotating plate, and engaging with the motor gear, and
the magnet rotates around the orthogonal axis direction with a rotation of the motor gear and the rotating plate gear due to a rotation of the motor, and
the magnet rotates around the rotation shaft by rotating and moving the rotation shaft gear on the fixed plate gear with the rotation of the magnet around the orthogonal axis direction.

2. The magnetic health device according to claim 1, wherein the frame is configured to support the magnet, the first rotation mechanism and the second rotation mechanism on both sides of a head.

* * * * *